(12) United States Patent
Shimoyama et al.

(10) Patent No.: US 7,248,908 B2
(45) Date of Patent: Jul. 24, 2007

(54) METHOD FOR MEASURING THE CONCENTRATION OF A SUBSTANCE IN A LIVING BODY AND DEVICE FOR MEASURING THE SAME CONCENTRATION

(75) Inventors: Isao Shimoyama, Nerima-ku (JP); Kiyoshi Matsumoto, Chiba (JP); Sumito Nagasawa, Bunkyo-ku (JP)

(73) Assignee: University of Tokyo, Tokyo (JP)

( * ) Notice: Subject to any disclaimer, the term of this patent is extended or adjusted under 35 U.S.C. 154(b) by 343 days.

(21) Appl. No.: 10/859,127

(22) Filed: Jun. 3, 2004

(65) Prior Publication Data

US 2005/0013779 A1    Jan. 20, 2005

(30) Foreign Application Priority Data

Jun. 6, 2003    (JP) ............................. 2003-162418

(51) Int. Cl.
*A61B 5/00*    (2006.01)
(52) U.S. Cl. ..................................... 600/317
(58) Field of Classification Search ................ 600/309, 600/310, 317, 329
See application file for complete search history.

(56) References Cited

U.S. PATENT DOCUMENTS 4,640,689 A * 2/1987 Sibalis ........................ 604/20
5,186,173 A * 2/1993 Zuckerman .................. 600/329
5,342,789 A * 8/1994 Chick et al. ................. 600/322
6,454,710 B1 * 9/2002 Ballerstadt et al. ......... 600/365
7,096,053 B2 * 8/2006 Loeb et al. .................. 600/317

FOREIGN PATENT DOCUMENTS

| JP | A 04-131746 | 5/1992 |
|---|---|---|
| JP | A-09-276275 | 10/1997 |
| JP | A-11-155812 | 6/1999 |
| JP | A-2000-300509 | 10/2000 |

OTHER PUBLICATIONS

Akiyuki Takahashi et al.; "Measurement of Intracellular Calcium"; Departments Of Cellular and Structural Biology and of Physiology, and Department of Molecular Medicine, Institute of Biotechnology, University of Texas Health Science Center at San Antonio, San Antonio, Texas; The American Physiological Society; *Physiological Reviews;* vol. 79; No. 4; Oct. 1999; 0031-93333/99; pp. 1089-1125.

(Continued)

*Primary Examiner*—Eric F Winakur
(74) *Attorney, Agent, or Firm*—Oliff & Berridge, PLC

(57) ABSTRACT

A fluorescence indicator is injected into a living body from a container via an injecting inlet to be chemically reacted with a substance in the living body. Then, an excitation light is irradiated to the living body from an excitation light source. Then, the thus obtained reflected light is reflected multiply at an reflective film formed on the inner wall of the container, and introduced into a detecting section, where a fluorescence response originated from the chemical bond between the substance and the fluorescence indicator and contained in the reflected light is detected.

29 Claims, 11 Drawing Sheets

OTHER PUBLICATIONS

Dermot Diamond et al.; "Robust Estimation of Selectivity Coefficients Using Multivariate Calibration of Ion-Selective Electrode Arrays"; School of Chemical Sciences, Dublin City University, Glasnevin, Dublin 9 (Ireland); Elsevier Science Publishers B.V.; *Analytica Chimica Acta;* 276; 1993; 0003-2670/93; pp. 75-86.

N. Fertig et al.; "Microstructured Glass Chip for Ion-Channel Electrophysiology"; Center for NanoScience and Sektion Physik et al.; The American Physical Society; *Physical Review E;* vol. 64; 2001; pp. 040901—040901-4.

Oliver T. Guenat et al; "Ion-Selective Microelectrode Array for Intracellular Detection on Chip"; Sensors, Actuators and Microsystems Laboratory, Institute of Microtechnology, University of Neuchatel et al; *Transducers '03*; The 12th International Conference on Solid State Sensors, Actuators and Microsystems, Boston, Jun. 8-12, 2003; pp. 1063-1066.

Weihong Tan et al.; "Submicrometer Intracellular Chemical Optical Fiber Sensors"; Department of Chemistry, University of Michigan, Ann Arbor, Michigan; *Science;* vol. 258; Oct. 30, 1992; pp. 778-781.

Todd A. Dickinson et al.; "A Chemical-Detecting System Based on a Cross-Reactive Optical Sensor Array"; The Max Tishler Laboratory for Organic Chemistry, Department of Chemistry, Tufts University et al.; *Nature;* vol. 382; Aug. 22, 1996; pp. 697-700.

Jianzhong Lu et al.; "Nanoscale Fluorescent Sensors for Intracellular Analysis", University of New Orleans, Department of Chemistry; *Fresenius J Anal Chem* (2000) vol. 366; pp. 569-575.

Sumito Nagasawa et al.; "Calcium Concentration Measurement by Local Flourescent-Dye Injection", *Sensors and Actuators*(2004) vol. 102; pp. 7-13.

\* cited by examiner

FIG. 4
(a)
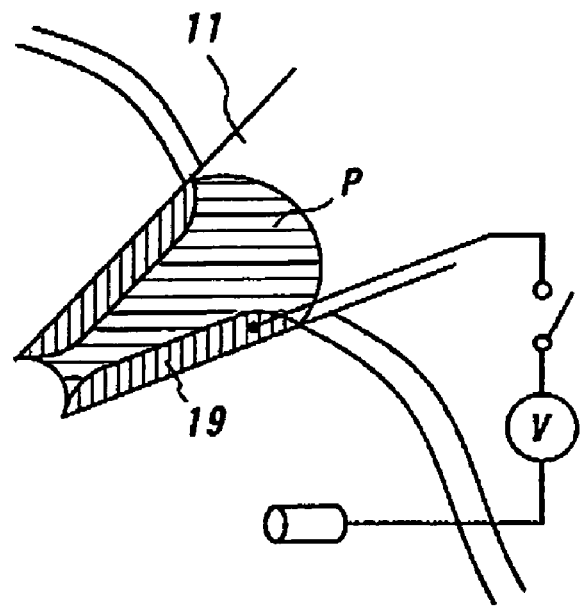
(b)
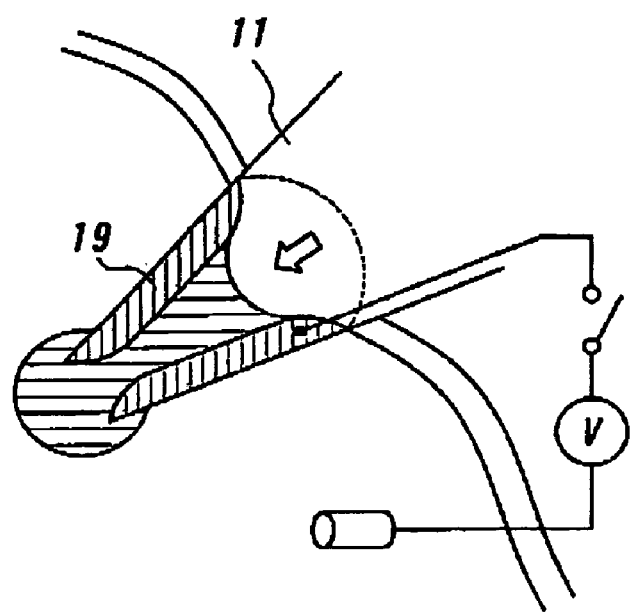

METHOD FOR MEASURING THE CONCENTRATION OF A SUBSTANCE IN A LIVING BODY AND DEVICE FOR MEASURING THE SAME CONCENTRATION

BACKGROUND OF THE INVENTION

1. Field of the Invention

This invention relates to a method for measuring the concentration of a substance in a minute region of a living body and a device for measuring the same concentration.

2. Description of the Related Art

In a conventional measuring method and a measuring device of the concentration of a substance in a living body, some tissues are taken out as a sample of the living body, and some fluorescence indicators to be chemically reacted with the living body are added to the sample so that by detecting the fluorescence response from the fluorescence indicators with a CCD camera, the concentration of the substance in the living body is measured. In this case, since the CCD camera is employed so that the fluorescence response can be measured as an image, the concentration distribution of the substance can be measured over the sample.

Generally, the sample is obtained by slicing the living body, but in the use of a confocal microscope, since the focus can be matched to a given depth by controlling the focal length, a bulky sample may be employed without slicing.

In the conventional measuring method and measuring device of the substance concentration, however, since the sample is taken out of the living body, the condition of the sample may be different from the condition that the sample remains in the living body. Moreover, since the fluorescence indicators are added over the sample, the sample can not be held for a long time after the substance concentration measurement, so that the successive measurement of the fluorescence response from the sample can not be performed.

In this point of view, instead of preparing the sample by slicing the living body, such an attempt is made as to insert a measuring probe directly into the living body and to measure the fluorescence response directly from the living body. In this case, however, a complicated optical alignment is required.

SUMMERY OF THE INVENTION

It is an object of the present invention to provide a method for measuring the concentration of a substance in a living body directly without taking out a sample of the living body, and a device for measuring the same concentration.

For achieving the above object, this invention relates to a method for measuring a concentration of a substance in a living body, comprising the steps of:

injecting a fluorescence indicator into a given living body,
irradiating and reflecting an excitation light to and from said living body to obtain a reflected light, and
detecting a fluorescence response originated from a chemical bond between the florescence indicator and a substance to be measured in concentration and contained in the reflected light to measure a concentration of the substance in the living body,
wherein the fluorescence response contained in the reflected light is detected in an injecting direction of the fluorescence indicator.

According to the present invention, a fluorescent indicator is directly injected into a living body to be measured in the substance concentration, and an excitation light is irradiated onto the fluorescent indicator injected region to detect the fluorescence response originated from the chemical bond between the substance of the living body and the fluorescence indicator and contained in the obtained reflection light from the excitation light. Therefore, the substance concentration of the living body can be measured in real time without taking out a sample of the living body on the condition that the substance remains in the living body. Moreover, since a measuring probe to be inserted is not required, the optical alignment can be simplified.

Since the fluorescence response in the reflection light is detected in the injecting direction of the fluorescence indicator, the fluorescence response can be detected high effectively from the measuring region of the living body so that the detection accuracy of the substance concentration can be enhanced.

Other features and advantages of the present invention will be described in detail hereinafter. Also, the measuring device of substance concentration of the present invention will be described in detail hereinafter.

BRIEF DESCRIPTION OF THE DRAWINGS

For better understanding of the present invention, reference is made to the attached drawings, wherein FIG. 4 is an explanatory view for still another injection of a florescence indicator into the living body.

DESCRIPTION OF THE PREFERRED EMBODIMENTS

This invention will be described in detail hereinafter.

Figure 1:
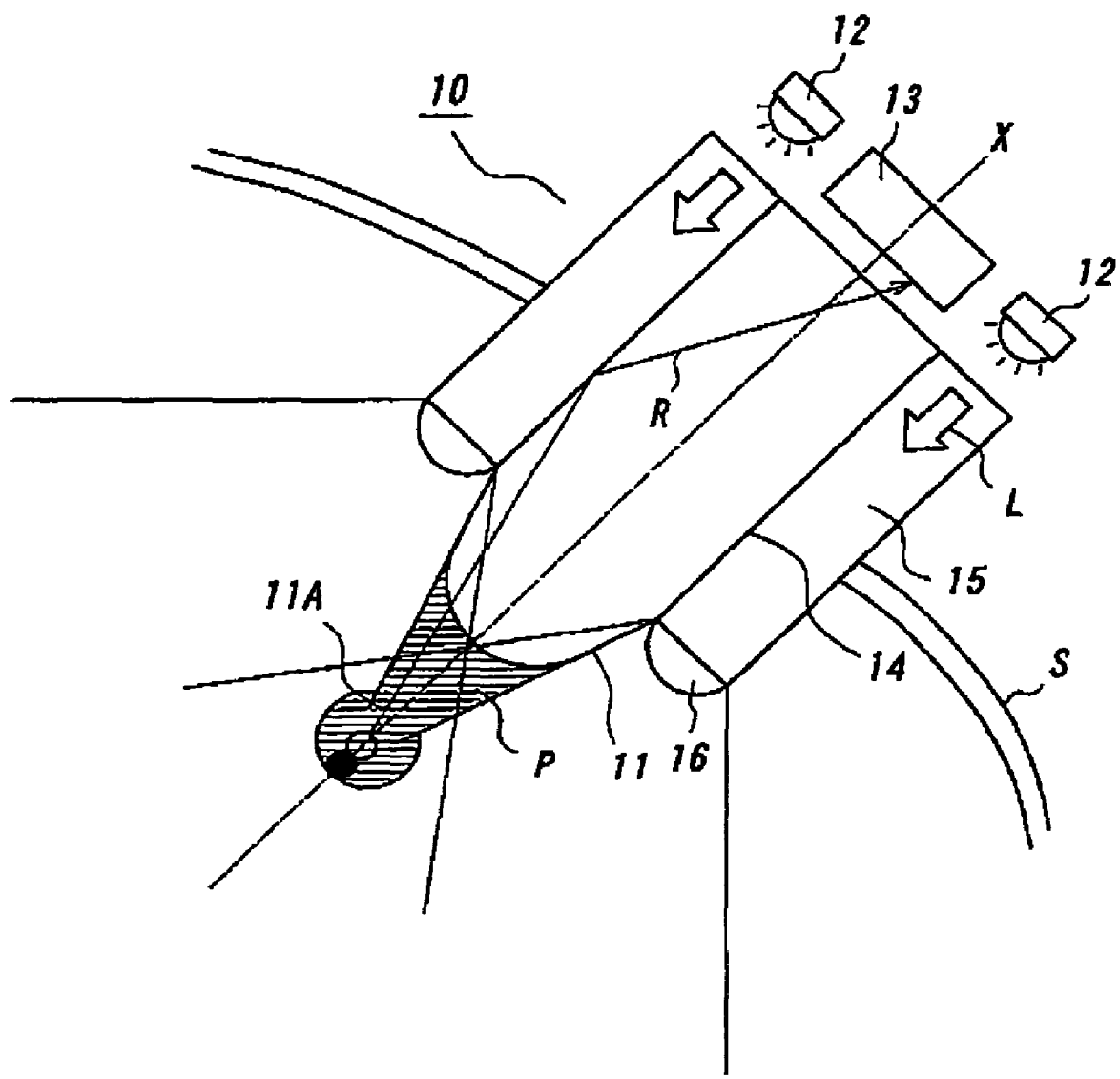
FIG. 1 is a structural view illustrating a measuring device of substance concentration for a living body according to the present invention.

FIG. 1 is a structural view illustrating a measuring device of substance concentration for a living body according to the present invention. The substance concentration measuring device 10 illustrated in FIG. 1 includes a container 11 to retain a fluorescence indicator P, an excitation light source 12 and a detecting section 13 which are provided in the rear side of the container 11. A reflective film 14 is formed on the inner wall of the container 11. A ring-shaped optical waveguide 15 is provided on the periphery of the container 11, and an optical scattering instrument 16 is provided on the forefront of the optical waveguide 15. An injecting outlet 11A is provided so as to be opposed to the living body S to be measured in substance concentration so that the fluorescence indicator P can be injected into the living body S. The detecting section 13 is disposed on the line X passing through the center of the injecting outlet 11A.

The container 11 may be made of glass or stainless steel, and the excitation light source 12 may be composed of a halogen lamp or a laser device which is commercially available. The detecting section 13 may be composed of an imaging device such as a CCD camera which is commercially available.

In the use of the measuring device illustrated in FIG. 1, the substance concentration in the living body S is measured as follows.

First of all, the fluorescence indicator P is injected into the living body S from the container 11 to be chemically bonded with the intended substance to be measured in concentration. Herein, only the fluorescence indicator P may be injected directly into the living body S. Or the fluorescence indicator P may be injected as a given solution into the living body S.

Then, an excitation light L is emitted from the excitation light source 12. The excitation light L is introduced to the optical scattering instrument 16 through the optical waveguide 15, and the thus scattered excitation light L is irradiated to the measuring region in living body S. The excitation light L is reflected at the measuring region in living body S, and the thus obtained reflected light R is introduced into the container 11 via the injecting outlet 11A. The reflected light R is reflected multiply at the reflective film 14 formed on the inner wall of the container 11, and introduced into the detecting section 13.

Since the reflected light R includes a fluorescence response originated from the chemical bond between the substance in the living body S and the fluorescence indicator P and obtained through the irradiation of the excitation light L in the measuring region of the living body S to which the fluorescence indicator P is injected, the fluorescence response of the reflected light R is detected at the detecting section 13. Since the fluorescence response is proportional to the binding ratio between the substance in the living body S and the fluorescence indicator P, if the fluorescence indicator P is injected sufficiently, to the concentration of the substance in the living body S, by detecting the fluorescence response, the concentration of the substance in the living body S can be measured.

In the measuring device illustrated in FIG. 1, since the detecting section 13 is disposed on the line X passing through the center of the injecting outlet 11A of the container 11, the fluorescence response in the measuring region of the living body S can be detected high effectively, and thus, the measuring accuracy of the substance concentration can be enhanced.

Figure 2:
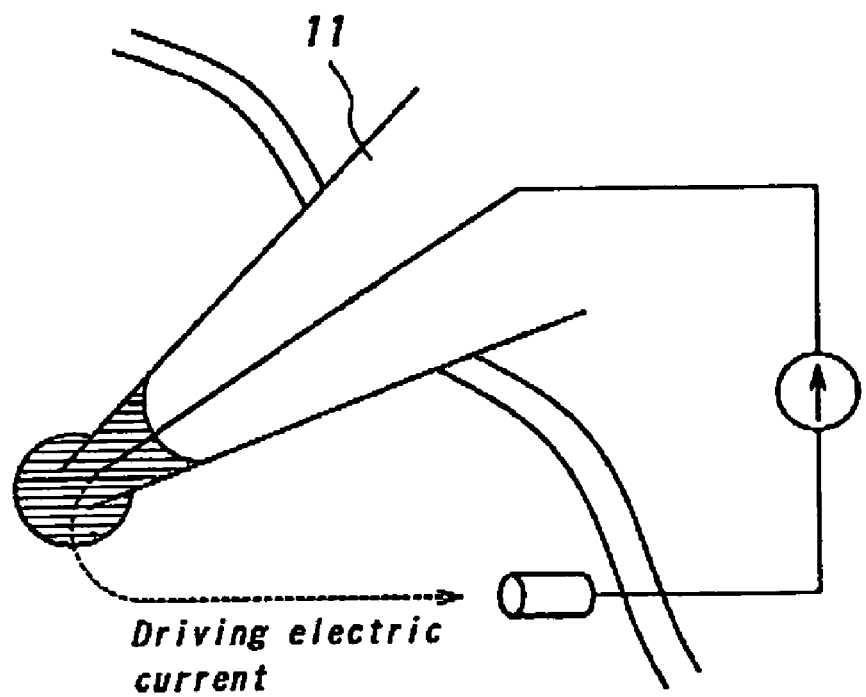
FIG. 2 is an explanatory view for an injection of a fluorescence indicator into the living body.
Figure 3:
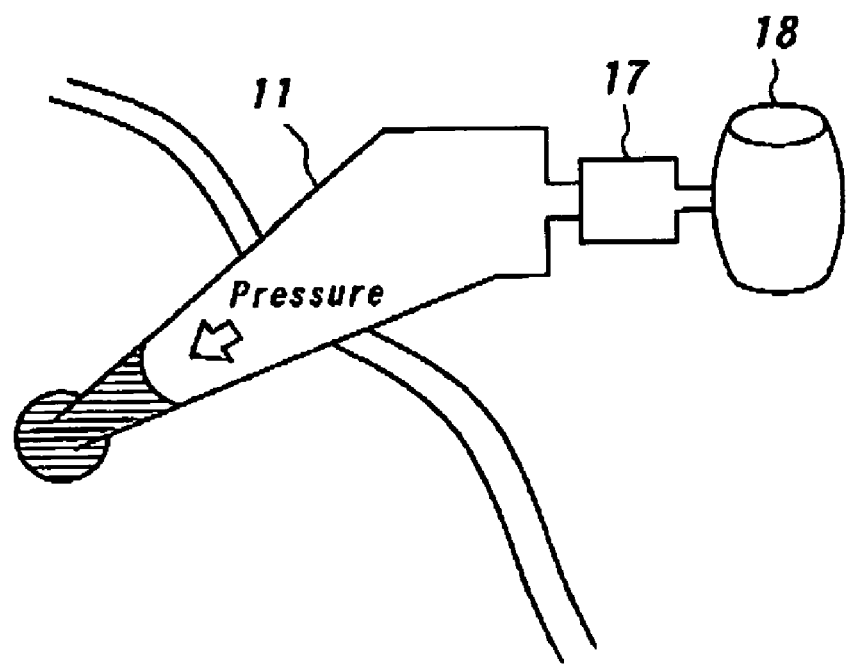
FIG. 3 is an explanatory view for another injection of a fluorescence indicator into the living body.

FIGS. 2-4 are explanatory views for injections of the fluorescence indicator P into the living body S. In FIG. 2, a difference in potential is generated between the fluorescence indicator P and the living body S to generate an ion flow or electric infiltration flow of the fluorescence indicator P, and the fluorescence indicator P is injected as the ion flow or the electric infiltration flow into the living body S.

In FIG. 3, a pressure source 18 is provided at the end of the container 11 via a valve 17, and a given pressure is added to the fluorescence indicator P in the container 11 from the pressure source 18. In this case, the fluorescence indicator P is discharged from the injecting outlet 11A, and injected into the living body S.

In FIG. 4, the florescence indicator P is retained in a given solution in the container 11, and the hydrophilic and the hydrophobic of the solution is controlled by applying a given voltage to the solution via an electrode 19. In this case, the fluorescence indicator P is discharged from the injecting outlet 11A through the volume change of the solution depending on the hydrophilic-hydrophobic change, and injected into the living body S.

In this embodiment, as illustrated in FIG. 4(a), at no application of the voltage, the solution exhibits hydrophilic, and thus, be expanded. Then, as illustrated in FIG. 4(b), at the application of the voltage, the solution exhibits hydrophobic, and thus, be shrunk. Therefore, the solution containing the fluorescence indicator P is discharged from the injecting outlet 11A of the container 11 through the expansion and shrinkage of the solution, and injected into the living body S.

The injections of the fluorescence indicator P are not restricted to the embodiments illustrated in FIGS. 2-4, but any other injection may be available.

The injecting amount of the fluorescent indicator P into the living body S can be monitored as follows. For example, in the use of the voltage application as illustrated in FIG. 2, the electric current amount between the living body S and the fluorescence indicator P is proportional to the ion flow or the electric infiltration flow of the fluorescence indicator P to be injected into the living body S. Therefore, by measuring the electric current amount, the injecting amount of the fluorescence indicator P can be monitored indirectly.

Moreover, another fluorescence indicator not to be chemically reacted with the substance in the living body is prepared and injected into the living body S with the fluorescence indicator P, and the fluorescence response from the additional fluorescence indicator is detected. If the additional fluorescence indicator is mixed uniformly with the fluorescence indicator P, since the additional fluorescence indicator P is injected into the living body S at a uniform ratio to the fluorescence indicator P, by measuring the fluorescence response from the additional fluorescence indicator, the injecting amount of the fluorescence indicator p can be determined and monitored indirectly.

Figure 5:
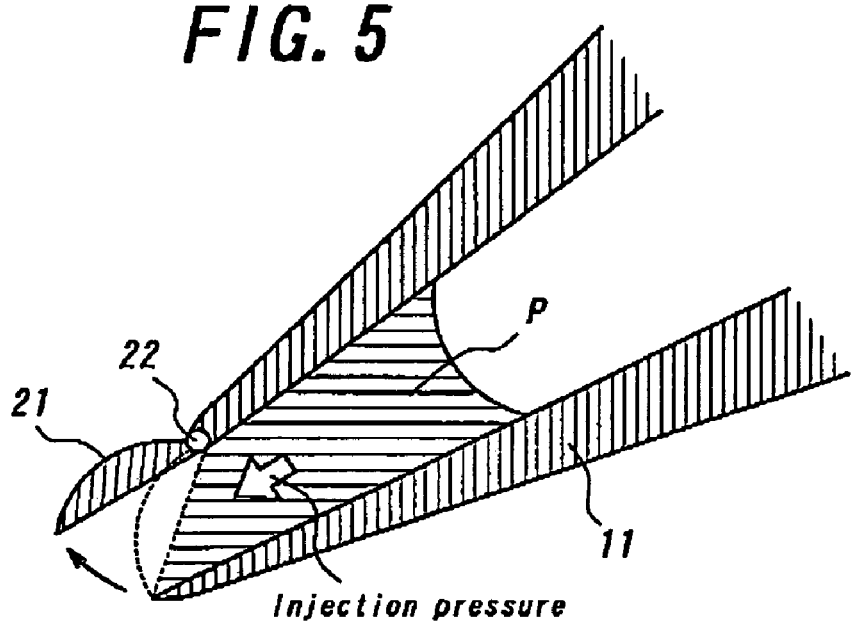
FIG. 5 is an explanatory view for a control of the injection amount of the fluorescence indicator.
Figure 6:
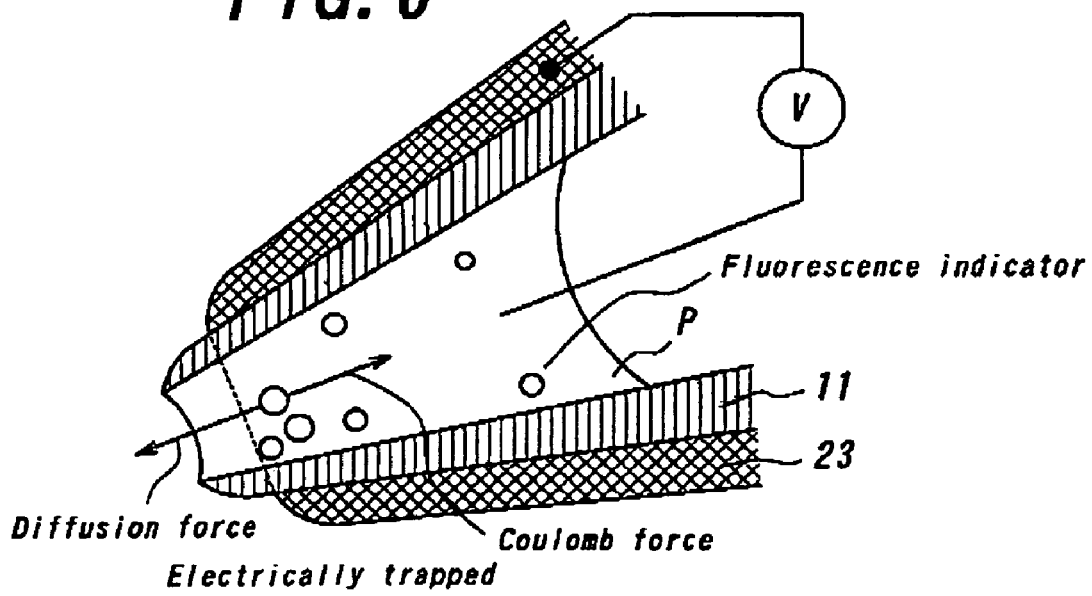
FIG. 6 is an explanatory view for another control of the injection amount of the fluorescence indicator.

FIGS. 5 and 6 are explanatory views for controls of the injection amount of the fluorescence indicator P into the living body S.

In the measurement using the measuring device as illustrated in FIG. 1, it may be required to control the injecting amount of the fluorescence indicator P into the living body S, in addition to the monitor thereof. In this case, for example as illustrated in FIG. 5, a shatter 21 is mounted on the injecting outlet 11A of the container 11 via a hinge 22, and through the open-close operation of the shatter 21, the discharging amount of the fluorescence indicator P from the injecting outlet 11A can be controlled, and thus, the injecting amount of the fluorescence indicator P into the living body S can be controlled. In FIG. 5, the open-close degree of the shatter 21 is controlled by adjusting the pressure to be added to the fluorescence indicator P, that is, the injecting pressure, and thus, the injecting amount of the fluorescence indicator P can be controlled.

Moreover, as illustrated in FIG. 6, an electrode 23 is provided on the periphery of the container 11, and a given voltage is applied to the fluorescence indicator P from the electrode 23. In this case, the discharging amount of the fluorescence indicator P from the injecting outlet 11A of the container 11 can be controlled by adjusting the strength and direction of the electrostatic force to the fluorescence indicator P, and thus, the injecting amount of the fluorescence indicator P into the living body S can be controlled.

The controls of the injecting amount of the fluorescence indicator P are not restricted to the examples illustrated in FIGS. 5 and 6, but any other injection may be available.

Figure 7:
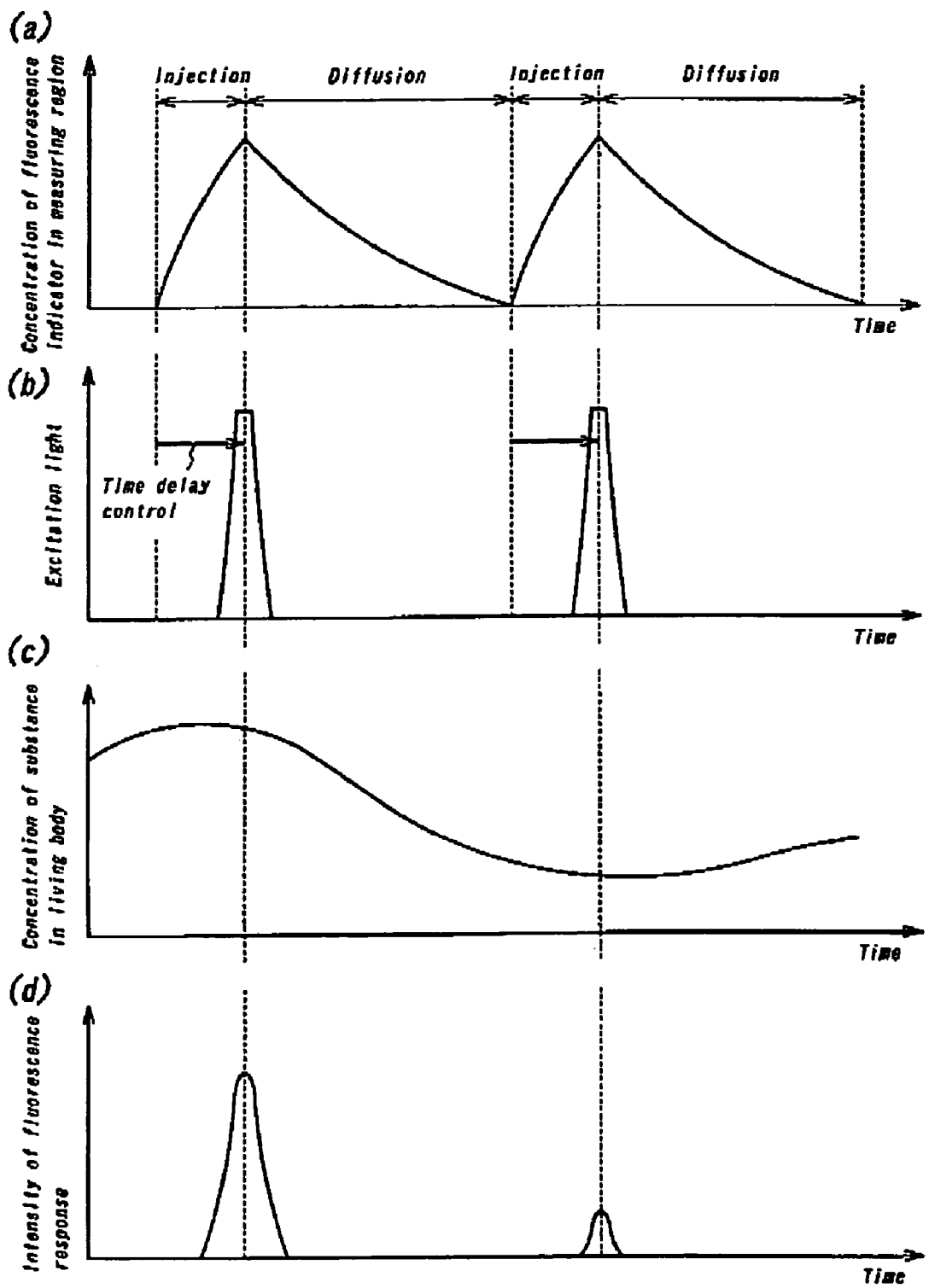
FIG. 7 is an explanatory view for a detection of the fluorescence response from the fluorescence indicator at the detecting section of the substance concentration measuring device of the present invention.

Then, the detecting method of the fluorescence response at the detecting section 13 will be described as follows. FIG. 7 is an explanatory view for a detection of the fluorescence response from the fluorescence indicator P at the detecting section 13.

As illustrated in FIG. 7(a), as soon as the fluorescence indicator P is injected into the living body S, the concentration of the fluorescence indicator P is increased, but thereafter, is decreased with time through diffusion. As illustrated in FIG. 7(a), therefore, when the injection and the diffusion of the fluorescence indicator P are alternately conducted, as illustrated in FIG. 7(b), it is desired that the irradiation of the excitation light L to the living body S is synchronized with the injection of the fluorescence indicator P. For example, the excitation light L is irradiated when the concentration of the fluorescence indicator P becomes maximum in the measuring region.

In this case, as illustrated in FIG. 7(c), even though the concentration of the substance to be measured in the living body S is changed, as illustrated in FIG. 7(d), the intensity of the fluorescence response can reflect the concentration change of the substance in the living body S because the fluorescence response is detected at the maximum and uniform concentration of the fluorescence indicator P. Therefore, the measuring accuracy of the substance concentration in the living body S can be enhanced.

Figure 8:
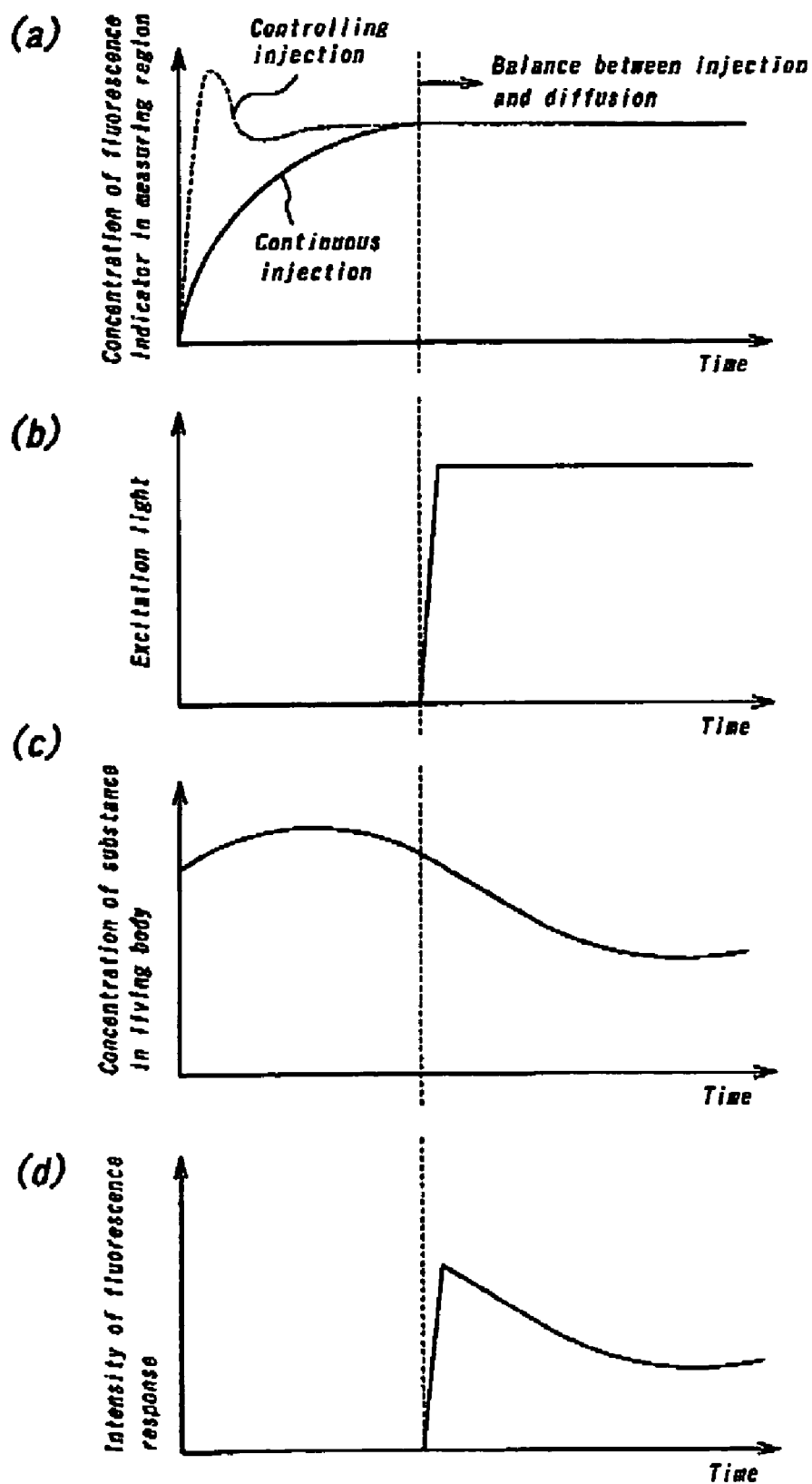
FIG. 8 is an explanatory view for another detection of the fluorescence response from the fluorescence indicator at the detecting section of the substance concentration measuring device of the present invention.

FIG. 8 is an explanatory view for another detection of the fluorescence response from the fluorescence indicator P at the detecting section 13. In this embodiment, as illustrated in FIG. 8(a), the fluorescence indicator P is injected continuously into the living body S so that the injection of the fluorescence indicator P is equal to the diffusion of the fluorescence indicator P to render the concentration of the fluorescence indicator P in the measuring region uniform. Then, as illustrated in FIG. 8(b), when the concentration of the fluorescence indicator P becomes uniform in the measuring region, the excitation light L is irradiated to the living body S, and thus, the concentration change of the substance in the living body S as illustrated in FIG. 8(c) can be detected as the intensity change of the fluorescence response as illustrated in FIG. 8(d). In this case, the measuring accuracy of the substance concentration in the living body S can be enhanced.

Figure 9:
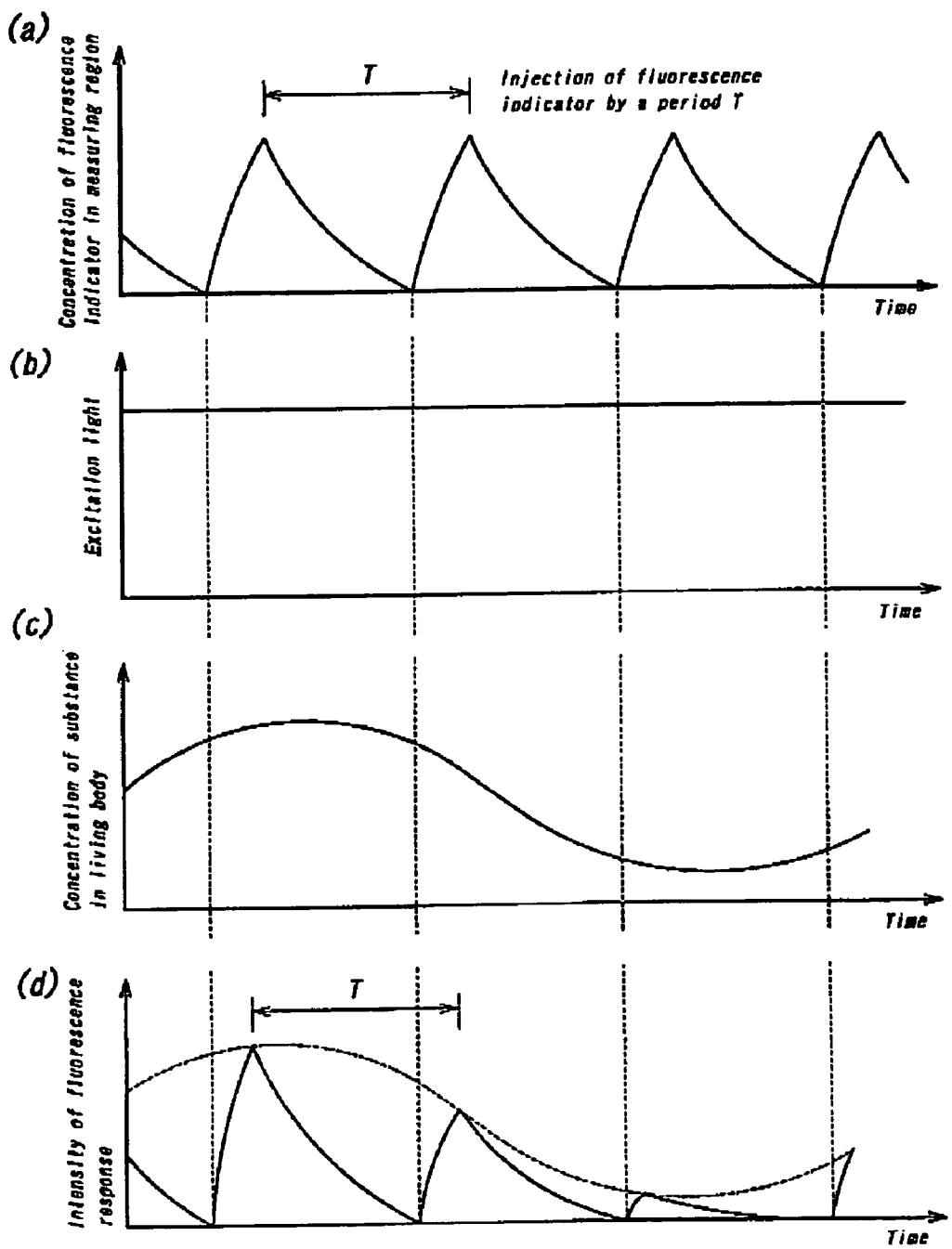
FIG. 9 is an explanatory view for still another detection of the fluorescence response from the fluorescence indicator at the detecting section of the substance concentration measuring device of the present invention.

FIG. 9 is an explanatory view for still another detection of the fluorescence response from the fluorescence indicator P at the detecting section 13. In this embodiment, as illustrated in FIG. 9(a), the injecting amount of the fluorescence indicator P is modulated by a period T, and as illustrated in FIG. 9(b), the excitation light L is irradiated continuously. In this case, as illustrated in FIG. 9(d), the intensity of the fluorescence response reflects the concentration change of the substance to be measured in the living body S and the injection period T of the fluorescence indicator P. Therefore, the measuring accuracy of the substance concentration in the living body S can be enhanced.

Figure 10:
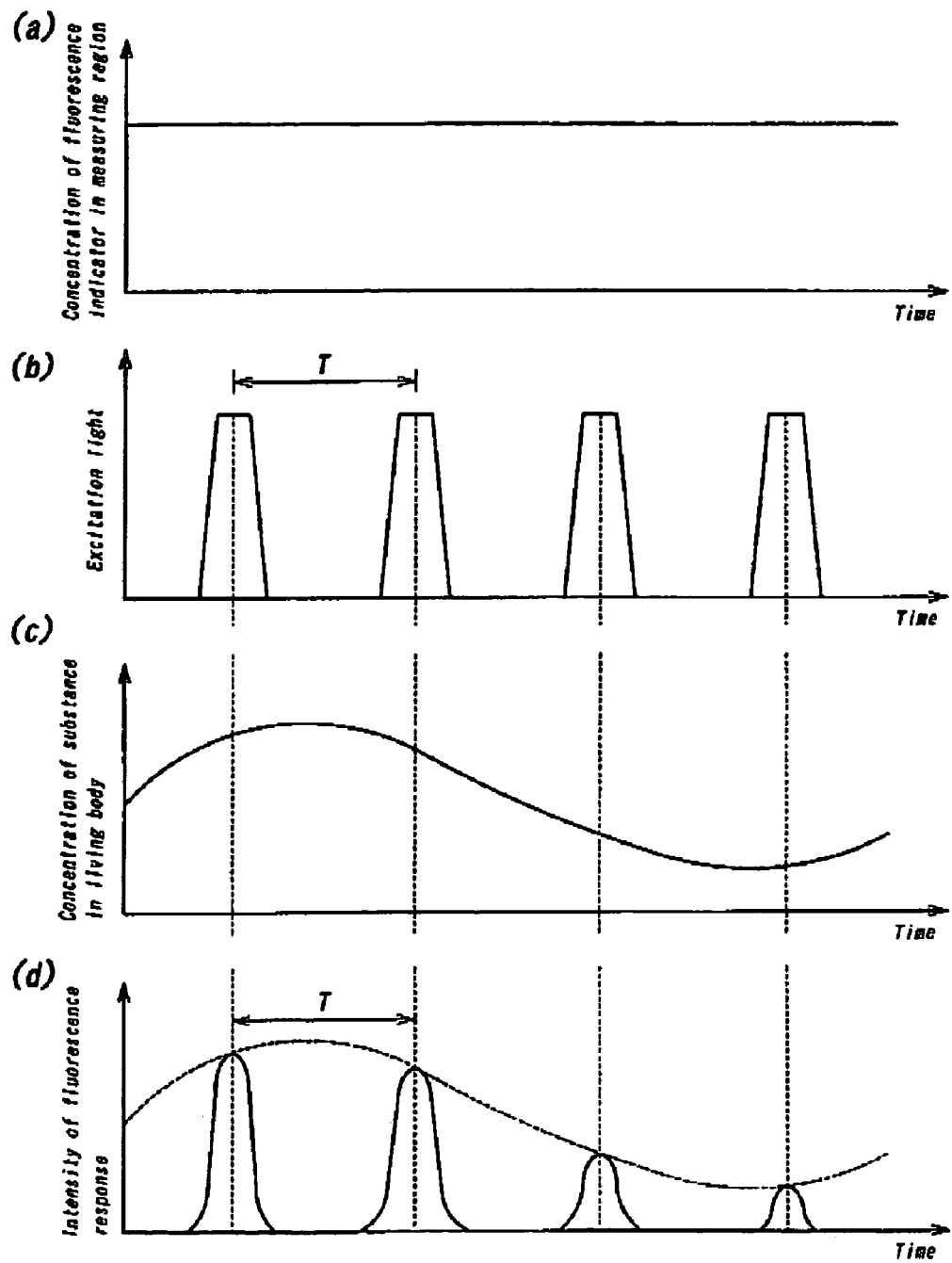
FIG. 10 is an explanatory view for a detection modified from the detection illustrated in FIG. 9.

FIG. 10 is an explanatory view for a detection modified from the detection illustrated in FIG. 9. In this embodiment, as illustrated in FIG. 10(a), the concentration of the fluorescence indicator P is maintained uniform in the measuring region of the living body S, and as illustrated in FIG. 10(b), the excitation light L is irradiated to the living body S at the period T. In this case, therefore, as illustrated in FIG. 10(d), the intensity of the fluorescence response reflects the concentration change of the substance in the living body S as illustrated in FIG. 10(c) and the irradiation period T of the excitation light L. Therefore, the measuring accuracy of the substance concentration in the living body can be enhanced.

Figure 11:
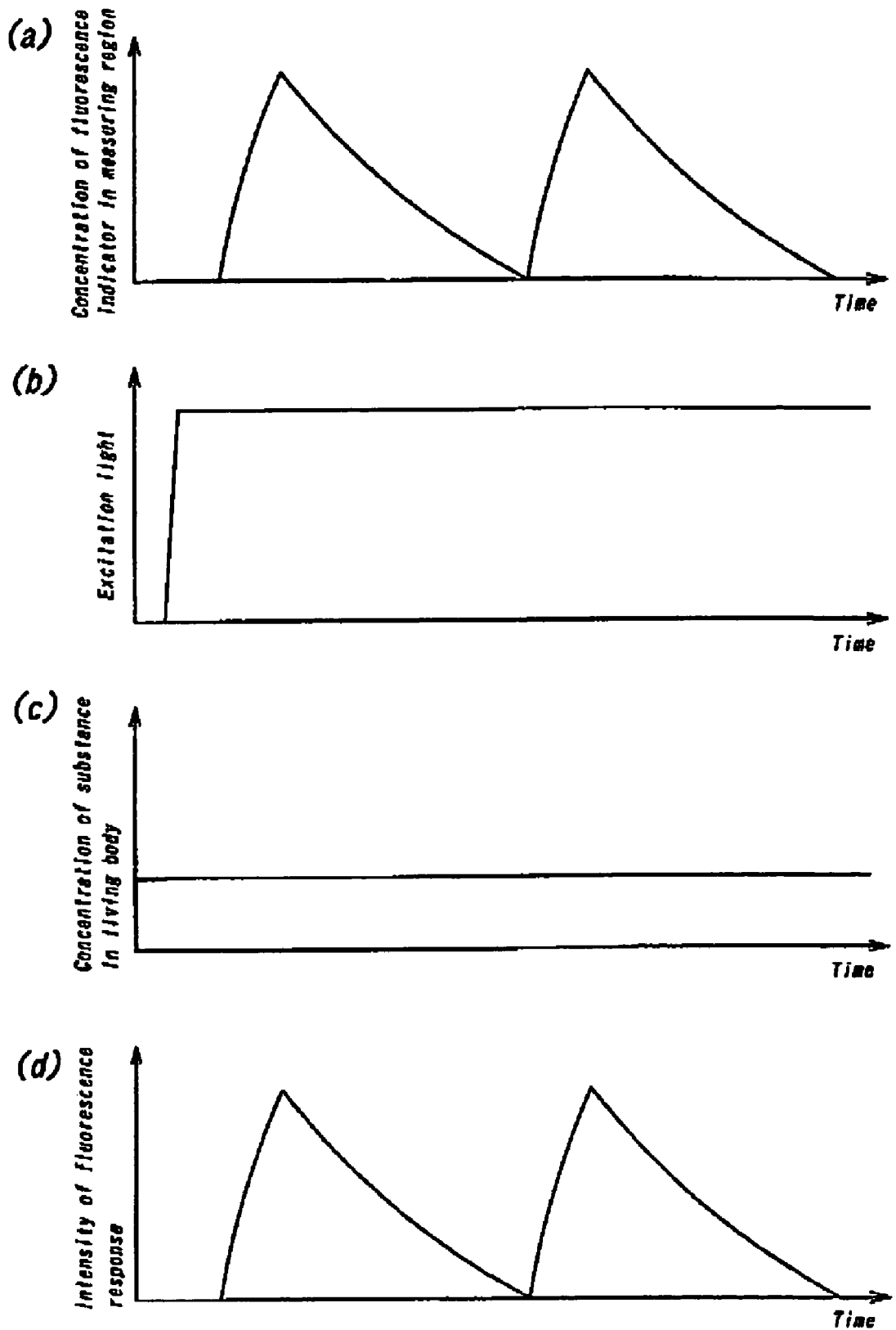
FIG. 11 is an explanatory view for a further detection of the fluorescence response from the fluorescence indicator at the detecting section of the substance concentration measuring device of the present invention.
Figure 12:
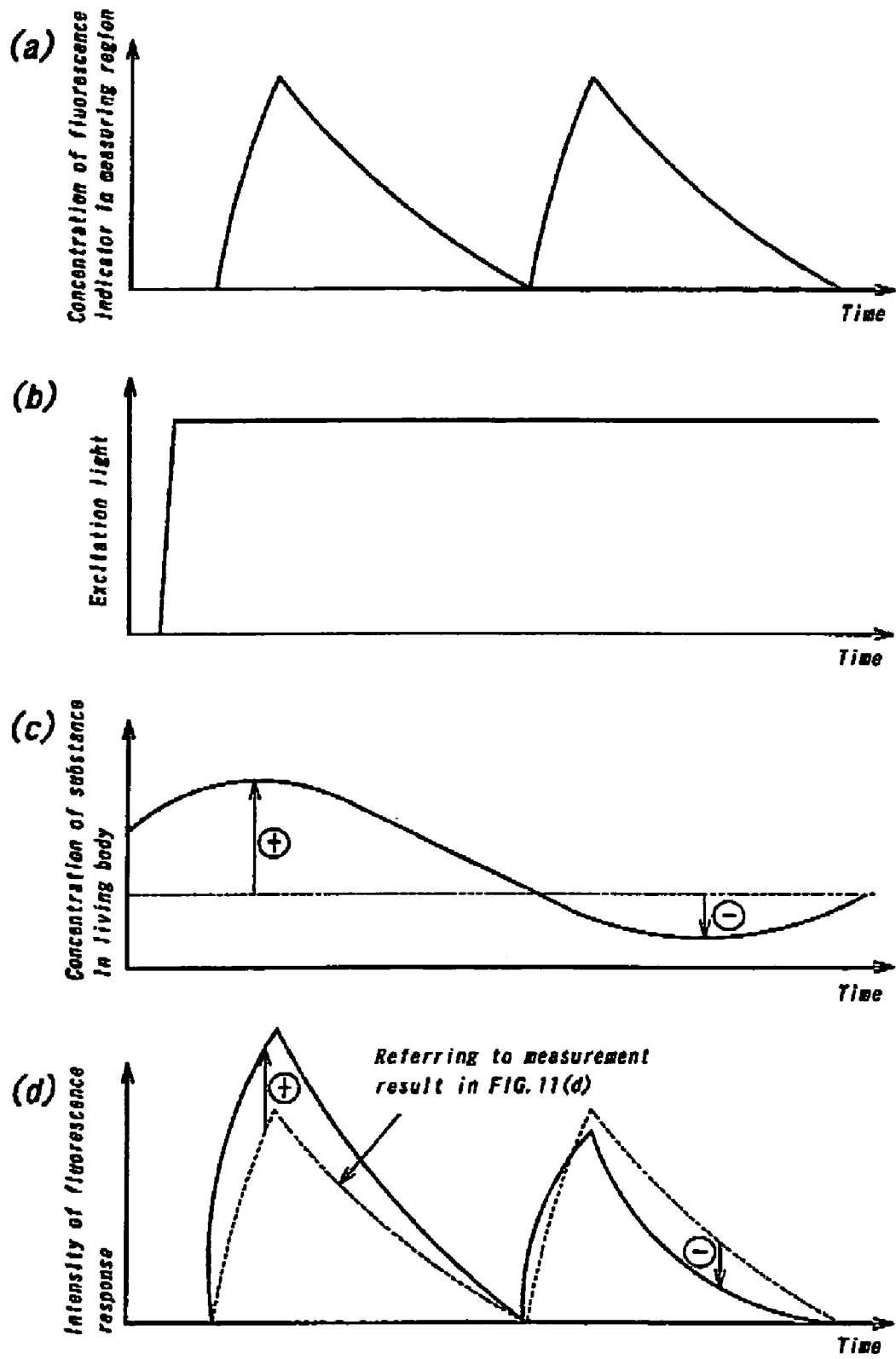
FIG. 12 is an explanatory view for a still further detection of the fluorescence response from the fluorescence indicator at the detecting section of the substance concentration measuring device of the present invention.

FIGS. 11 and 12 are explanatory views for other detections of the fluorescence response from the fluorescence indicator P at the detecting section 13. In this embodiment, the injection of the fluorescence indicator P and the detection of the fluorescence response are conducted in the same manner as illustrated in FIG. 9. The fluorescence indicator P is injected into the living body S by a given period under the condition as illustrated in FIG. 11(a), and the fluorescence response as illustrated in FIG. 11(d) is measured under the condition that the substance concentration in the living body S can be maintained uniform. Then, as illustrated in FIGS. 12(a) and 12(b), the injection period of the fluorescence indicator P and the irradiation of the excitation light L are set to the ones as illustrated in FIGS. 11(a) and 11(b), and as illustrated in FIG. 12(d), the intensity of the fluorescence response is measured under the condition that as illustrated in FIG. 12(c), the substance concentration is changed in the living body S.

Since the fluorescence response intensity illustrated in FIG. 12(d) includes the fluorescence response intensity at the static state where the substance concentration is not changed as illustrated in FIG. 11(c), if the fluorescence response intensity illustrated in FIG. 11(c) is subtracted from the fluorescence response intensity illustrated in FIG. 12(d), only the fluorescence response intensity due to the change of the substance concentration in the living body S can be detected.

Although the present invention was described in detail with reference to the above examples, this invention is not limited to the above disclosure and every kind of variation and modification may be made without departing from the scope of the present invention.

Figure 13:
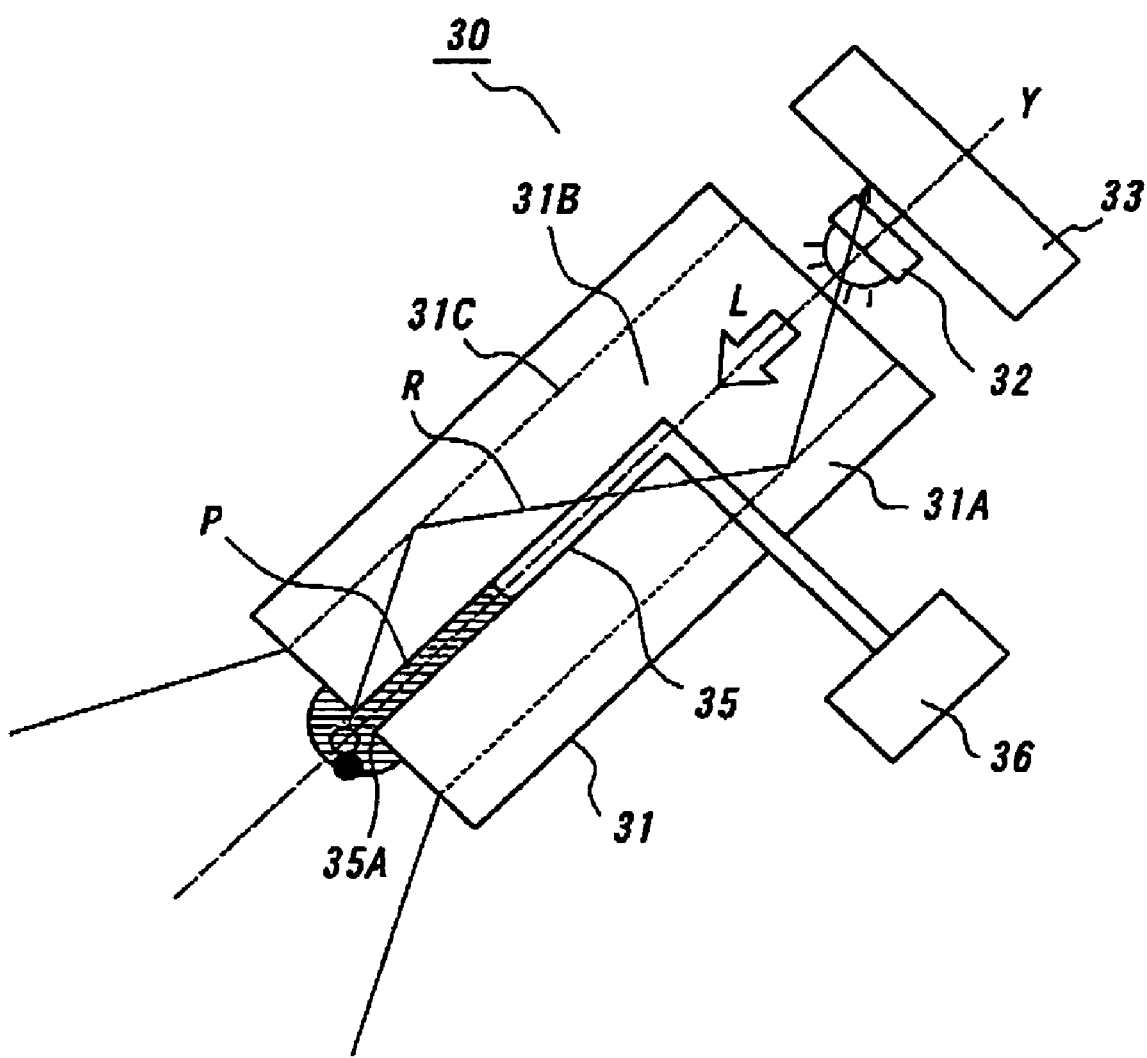
FIG. 13 is a structural view illustrating another measuring device of substance concentration for a living body according to the present invention.

FIG. 13 is a structural view illustrating another measuring device of substance concentration for a living body according to the present invention. The substance concentration measuring device 30 illustrated in FIG. 13 includes an optical fiber 31, an excitation light source 32, and a detecting section 33. In the optical fiber 31 is provided a guide 35 to introduce the fluorescence indicator P to the forefront 35A, and at the end of the guide 35 is provided a storage container 36 to retain the fluorescence indicator P. The detecting section 33 is disposed on the line Y passing through the center of the guide 35.

In the use of the measuring device illustrated in FIG. 13, the fluorescence indicator P is injected into a living body (not shown) from the forefront 35A of the guide 35. In this case, in the living body, the fluorescence indicator P is chemically reacted with the substance to be measured. Then, a given excitation light is irradiated to the living body through the optical fiber 31, and reflected. The thus obtained reflected light R is introduced into the optical fiber 31 from the forefront of the optical fiber 31, and reflected multiply at the interface 31C between the core 31A and the clad 31B of the optical fiber 31 to be introduced into the detecting section 33.

At the detecting section 33, the fluorescence response originated from the chemical bond between the fluorescence indicator P and the substance to be measured and contained in the reflected light R is detected, and the substance concentration in the living body S can be measured.

As described above, according to the present invention can be provided a method for measuring the concentration of a substance in a living body directly without taking out a sample of the living body, and a device for measuring the same concentration.

What is claimed is:

1. A method for measuring a concentration of a substance in a living body, comprising the steps of:
    injecting a fluorescence indicator into a given living body at an injecting outlet;
    irradiating and reflecting an excitation light to and from said living body to obtain a reflected light;
    detecting a fluorescence response originated from a chemical bond between said fluorescence indicator and a substance to be measured in concentration and contained in said reflected light to measure a concentration of said substance in said living body; and
    indicating the measured concentration;
    wherein said reflected light is collected through an optical waveguide having an opening placed coaxial with said injecting outlet.

2. The measuring method as defined in claim 1, wherein said fluorescence indicator is injected as an ion flow or an electric infiltration flow which is formed by a difference in potential between said fluorescence indicator and said living body.

3. The measuring method as defined in claim 2, further comprising the step of measuring an electric current originated from said ion flow or said electric infiltration flow of said fluorescence indicator to monitor an injecting amount of said fluorescence indicator into said living body.

4. The measuring method as defined in claim 1, wherein said fluorescence indicator is injected into the living body by means of pressurization.

5. The measuring method as defined in claim 1, wherein said fluorescence indicator is retained in a solution of which a hydrophilic and hydrophobic are controlled by applying a voltage to said solution, and said fluorescence indicator is injected into said living body by a volume expansion of said solution through hydrophilic-hydrophobic control.

6. The measuring method as defined in claim 1, further comprising the step of monitoring an injecting amount of said fluorescence indicator into said living body.

7. The measuring method as defined in claim 6, wherein said monitoring comprises the steps of:
    preparing an additional fluorescence indicator;
    injecting said additional fluorescence indicator into said living body with said fluorescence indicator; and
    measuring a fluorescence response from said additional fluorescence indicator to monitor said injecting amount of said fluorescence indicator.

8. The measuring method as defined in claim 1, further comprising the step of controlling an injecting amount of said fluorescence indicator into said living body.

9. The measuring method as defined in claim 8, wherein said injecting amount of said fluorescence indicator is controlled mechanically.

10. The measuring method as defined in claim 9, wherein said injecting amount of said fluorescence indicator is controlled with a shatter.

11. The measuring method as defined in claim 8, wherein said injecting amount of said fluorescence indicator is controlled electrically.

12. The measuring method as defined in claim 11, wherein said injecting amount of said fluorescence indicator is controlled by means of electrostatic force.

13. The measuring method as defined in claim 1, wherein said fluorescence indicator is retained in a container constituting said optical waveguide with said injecting outlet formed at a forefront thereof which is configured to penetrate said living body, and said reflected light is reflected multiply at an inner wall of said container prior to said detecting step.

14. The measuring method as defined in claim 13, wherein said excitation light is passed through a second optical waveguide formed at a periphery of said container, and introduced into an optical scattering instrument mounted at a forefront of said second optical waveguide to be irradiated to said living body.

15. The measuring method as defined in claim 1, wherein said excitation light is irradiated to said living body through an optical fiber constituting said optical waveguide, and said reflected light is reflected multiply at an interface between a clad and a core of said optical fiber prior to said detecting step.

16. The measuring method as defined in claim 15, wherein said fluorescence indicator is injected into said living body through a guide so formed as to penetrate said optical fiber.

17. The measuring method as defined in claim 1, wherein said injecting step is synchronized with said irradiation step.

18. The measuring method as defined in claim 17, wherein said irradiating step is performed when a concentration of said fluorescence indicator becomes uniform in a measuring region in said living body.

19. The measuring method as defined in claim 1, wherein at least one of said injecting and said irradiating is modulated by a given frequency.

20. The measuring method as defined in claim 1, wherein when said concentration of said substance is changed through an action of said substance, said method further comprising detecting a pre-fluorescence response in said living body at non-activity of said substance in advance, and during a subsequent measurement subtracting said pre-fluorescence response at said non-activity from said fluorescence response contained in said reflected light to detect a fluorescence response at activity of said substance.

21. A device for measuring a concentration of a substance in a living body, comprising:
    a container with an injecting outlet at a forefront thereof which is configured to penetrate a living body and to retain a fluorescence indicator to be injected into said living body;
    an excitation light source to irradiate an excitation light to said living body; and
    a detecting section to detect a reflected light from said living body;
    wherein said detecting section is disposed on a line passing through a center of said injecting outlet of said container, and said reflected light is collected through said injecting outlet of said container.

22. The measuring device as defined in claim 21, further comprising an electrode outside said container.

23. The measuring device as defined in claim 22, wherein a difference in potential is generated between said electrode and said living body to generate an ion flow or an electric infiltration flow of said fluorescence indicator, and said fluorescence indicator is injected as said ion flow or said electric infiltration flow into said living body.

24. The measuring device as defined in claim 22, wherein a difference in potential is generated between said electrode and said fluorescence indicator to control an injecting amount of said fluorescence indicator into said living body.

25. The measuring device as defined in claim 22, wherein said fluorescence indicator is retained in a solution of which a hydrophilic and hydrophobic properties are controlled by a difference in potential between said electrode and said solution, and said fluorescence indicator is injected into said living body by a volume expansion of said solution through hydrophilic-hydrophobic control.

26. The measuring device as defined in claim 21, further comprising a pressure source to inject said fluorescence indicator into said living body through pressurization.

27. The measuring device as defined in claim 21, further comprising a shatter at a forefront of said container, wherein an injecting amount of said fluorescence indicator into said living body is controlled with said shatter.

28. The measuring device as defined in claim 21, further comprising an optical waveguide with an optical scattering instrument at a forefront thereof outside said container.

29. A device for measuring a concentration of a substance in a living body, comprising:
   an excitation light source to irradiate an excitation light to a living body;
   an optical fiber to transmit said excitation light;
   a detecting section to detect a reflected light from said living body; and
   a storage container to retain a fluorescence indicator to be injected into said living body;
   wherein a guide to introduce said fluorescence indicator to a forefront of said optical fiber is formed in said optical fiber; and
   said detecting section is disposed on a line passing through a center of said guide, and said reflected light is collected through said forefront of said guide when positioned within said living body.

* * * * *